(12) United States Patent
Blanton et al.

(10) Patent No.: US 9,188,775 B2
(45) Date of Patent: Nov. 17, 2015

(54) OPTICAL SCANNING AND MEASUREMENT

(71) Applicant: UNITED SCIENCES, LLC, Atlanta, GA (US)

(72) Inventors: Keith A. Blanton, Alpharetta, GA (US); Karol Hatzilias, Atlanta, GA (US); Stefan T. Posey, Austell, GA (US); Wess Eric Sharpe, Vinings, GA (US)

(73) Assignee: United Sciences, LLC, Atlanta, GA (US)

( * ) Notice: Subject to any disclaimer, the term of this patent is extended or adjusted under 35 U.S.C. 154(b) by 0 days.

(21) Appl. No.: 14/094,130

(22) Filed: Dec. 2, 2013

(65) Prior Publication Data

US 2015/0062585 A1    Mar. 5, 2015

Related U.S. Application Data

(60) Provisional application No. 61/871,002, filed on Aug. 28, 2013.

(51) Int. Cl.
| | |
|---|---|
| *G01N 21/00* | (2006.01) |
| *G02B 26/08* | (2006.01) |
| *G01B 11/25* | (2006.01) |
| *G01B 11/12* | (2006.01) |
| *G01B 11/24* | (2006.01) |

(Continued)

(52) U.S. Cl.
CPC ............ *G02B 26/0875* (2013.01); *G01B 11/12* (2013.01); *G01B 11/24* (2013.01); *G01B 11/2408* (2013.01); *G01B 11/2518* (2013.01); *G01N 21/01* (2013.01); *G01N 21/55* (2013.01); *G01Q 10/00* (2013.01); *G07C 3/143* (2013.01); *G01N 2021/0181* (2013.01)

(58) Field of Classification Search
CPC ............... G01N 33/54373; G01N 21/4795; G01N 21/253; G01N 21/31; G01N 21/4788; G01N 21/636; G01N 21/7743; G01N 2333/726; G01N 2458/00; G01N 2500/02; G01N 2500/04; G01N 33/5308; G01N 33/54313
See application file for complete search history.

(56) References Cited

U.S. PATENT DOCUMENTS

| | | |
|---|---|---|
| 4,561,776 A | 12/1985 | Pryor |
| 4,839,526 A | 6/1989 | Pryor |

(Continued)

OTHER PUBLICATIONS

PCT Search Report and Written Opinion, May 28, 2014, PCT Application No. PCTUS2014015665, 13 pages.

(Continued)

*Primary Examiner* — Michael P Stafira
(74) *Attorney, Agent, or Firm* — H. Artoush Ohanian; United Sciences, LLC

(57) ABSTRACT

Apparatus and methods for optical scanning, including an optical probe capable of motion for optical scanning with respect to both the interior and the exterior of a scanned object, the optical probe also including light conducting apparatus disposed so as to conduct scan illumination from a source of scan illumination through the probe; light reflecting apparatus disposed so as to project scan illumination radially away from a longitudinal axis of the probe with at least some of the scan illumination projected onto the scanned object; optical line forming apparatus disposed so as to project scan illumination as a line of scan illumination with at least some of the scan illumination projected onto the scanned object; and a lens disposed so as to conduct, through the probe to an optical sensor, scan illumination reflected from the scanned object.

25 Claims, 8 Drawing Sheets

(51) Int. Cl.
  *G01N 21/55* (2014.01)
  *G01N 21/01* (2006.01)
  *G07C 3/14* (2006.01)
  *G01Q 10/00* (2010.01)

(56) References Cited

U.S. PATENT DOCUMENTS

| | | | |
|---|---|---|---|
| 4,967,092 | A | 10/1990 | Fraignier et al. |
| 5,254,859 | A | 10/1993 | Carman et al. |
| 5,557,438 | A | 9/1996 | Schwartz et al. |
| 5,804,830 | A | 9/1998 | Shafir |
| 5,859,364 | A | 1/1999 | Toda et al. |
| 6,181,411 | B1 | 1/2001 | Harris et al. |
| 6,657,216 | B1 * | 12/2003 | Poris ............ 250/559.22 |
| 6,758,564 | B2 * | 7/2004 | Ferguson ............ 351/221 |
| 7,009,717 | B2 | 3/2006 | Van Coppenolle et al. |
| 7,016,052 | B2 | 3/2006 | Bloch et al. |
| 7,027,145 | B2 | 4/2006 | Segall et al. |
| 7,129,472 | B1 * | 10/2006 | Okawa et al. ............ 250/234 |
| 7,251,366 | B1 | 7/2007 | Silver et al. |
| 7,329,860 | B2 * | 2/2008 | Feng et al. ............ 250/234 |
| 7,428,061 | B2 | 9/2008 | Coppenolle et al. |
| 7,534,995 | B2 | 5/2009 | Peters et al. |
| 7,903,245 | B2 | 3/2011 | Miousset et al. |
| 8,035,823 | B2 | 10/2011 | Keightley et al. |
| 8,467,071 | B2 | 6/2013 | Steffey et al. |
| 2003/0106378 | A1 | 6/2003 | Giannakopoulos et al. |
| 2007/0070340 | A1 | 3/2007 | Karpen |
| 2007/0229806 | A1 | 10/2007 | Lally et al. |
| 2007/0247639 | A1 | 10/2007 | Amstel et al. |
| 2007/0296964 | A1 | 12/2007 | Nishimura et al. |
| 2008/0062434 | A1 | 3/2008 | Diefenbacher |
| 2008/0106722 | A1 | 5/2008 | Shibazaki |
| 2008/0156619 | A1 | 7/2008 | Patel et al. |
| 2008/0283738 | A1 | 11/2008 | Peters et al. |
| 2009/0208143 | A1 * | 8/2009 | Yoon et al. ............ 382/321 |
| 2010/0060904 | A1 | 3/2010 | Keightley et al. |
| 2011/0211869 | A1 | 9/2011 | Shouji et al. |
| 2011/0313558 | A1 | 12/2011 | Lehman et al. |
| 2012/0184842 | A1 | 7/2012 | Boularot et al. |
| 2012/0190921 | A1 | 7/2012 | Yadlowsky et al. |
| 2012/0288336 | A1 | 11/2012 | Berg |
| 2013/0158393 | A1 | 6/2013 | Papac et al. |
| 2013/0218528 | A1 | 8/2013 | Lind et al. |
| 2013/0237754 | A1 | 9/2013 | Berglund et al. |

OTHER PUBLICATIONS

PCT Search Report and Written Opinion, May 28, 2014, PCT Application No. PCTUS2014015670, 12 pages.
PCT Search Report and Written Opinion, May 19, 2014, PCT Application No. PCTUS2014015674, 28 pages.
PCT Search Report and Written Opinion, May 23, 2014, PCT Application No. PCTUS2014015676, 18 pages.
Notice of Allowance, U.S. Appl. No. 13/737,017, May 29, 2014, pp. 1-12.
Notice of Allowance, U.S. Appl. No. 14/099,482, Aug. 29, 2014, pp. 1-12.
Devlieg et al., "Applied Accurate Robotic Drilling for Aircraft Fuselage", Technical paper, SAE 2010 Aerospace Manufacturing and Automated Fastening Conference & Exhibition, Sep. 2010, 8 pages, Society of Automotive Engineers (SAE) International, USA.
Office Action, U.S. Appl. No. 13/767,017, Dec. 17, 2013, pp. 1-10.

\* cited by examiner

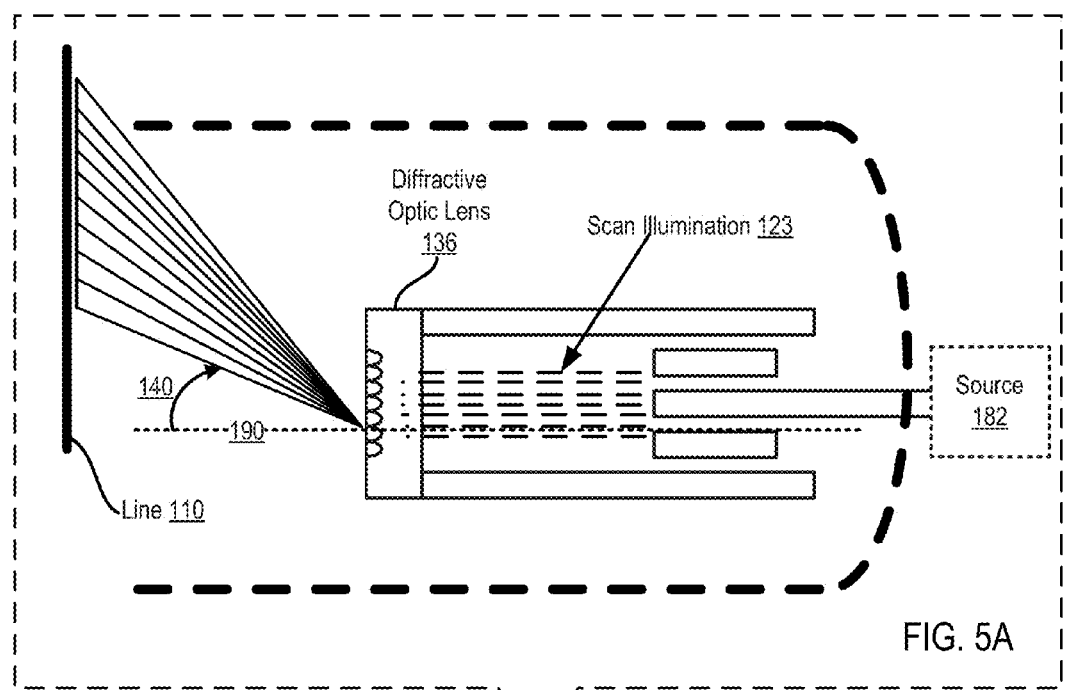
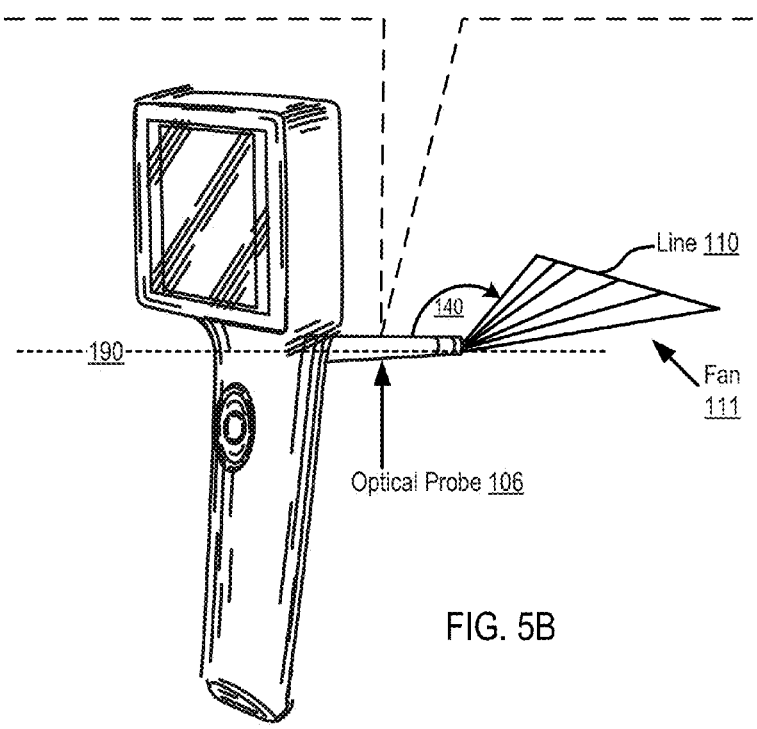

OPTICAL SCANNING AND MEASUREMENT

CROSS-REFERENCE TO RELATED APPLICATION

This patent application claims the benefit and priority of U.S. Provisional Patent Application No. 61/871,002, filed Aug. 28, 2013, and entitled "Optical Systems For Measuring A Drilled Hole In A Structure And Methods Relating Thereto."

BACKGROUND

Much research and manufacturing today requires precision metrology, very accurate measurement and inspection of mass produced and custom components, components in wind turbines, jet engines, combustion gas turbines, nuclear reactors, ships, automobiles, other aviation components, medical devices and prosthetics, 3D printers, plastics, fiber optics, other optics for telescopes, microscopes, cameras, and so on. The list is long, and the problems are large. In inspecting an airframe, for example, an inspection checks the diameter and circularity of each of thousands of holes at different depths to ensure that each hole is perpendicular to a surface, circular in cross section as opposed to elliptical, not conical, not hour-glass-shaped, and so on. Such inspections are performed by human quality assurance inspectors, who inspect large groups of holes at one time, extremely laboriously. When a drill bit or mill head becomes chipped or otherwise damaged, its current hole and all its potentially hundreds or thousands of subsequent holes are out of tolerance, none of which are identified until inspection.

Prior art attempts at high precision measurement include focal microscopy for fringe pattern analysis, that is image analysis by comparison with a pre-image of a correct part, all difficult to deploy and not very accurate. Other prior art includes capacitive probes such as described for example in U.S. 2012/0288336. Such capacitive probes, however, take measurements in only one direction at a time, requiring multiple measurements to assess a part, never assembling a complete image of the inside of a part. Moreover, a capacitive probe must fit tightly into or onto a part to be measured, aligned closely to the center axis of the hole, and for calibration purposes, must have the same probe-to-hole-side separation at all times—because its capacitance is calibrated according to the thickness of the layer of air between the probe and a component to be scanned or measured. When such a capacitive probe identifies a problem with a part, and the part is redrilled or remilled to a larger size, the capacitive probe must be swapped out to a larger diameter probe in order to remeasure the part.

Prior art optical scanners typically are too bulky to move with respect to a part under inspection. Such optical scanners are typically mounted on a fixture with a scanned part in a jig that moves with respect to the scanner. This fixed physical orientation between the optical scanner and a part to be scanned or measured means that there are always aspects of the part that cannot be reached, measured, scanned, or imaged by such a prior art optical scanner. This limitation of prior art has given rise to so-called multi-sensor metrology devices that include both optical scan capability and also tactile sensors that attempt to measure portions of a part that optical scan illumination cannot reach—all in an attempt to build a scanner that can scan a part accurately and completely. One manufacturer of metrology equipment, for example, combines three types of sensor probes, a light section sensor, a shape-from-focus (SFF) sensor, and a tactile sensor, all of which are said to work in unison to achieve optimum measurement, even in areas where scan illumination cannot reach. There continues in the industry some real need for an optical scanner with better reach.

BRIEF DESCRIPTION OF THE DRAWINGS

FIGS. 4A, 4B, 4C, 5A, and 5B illustrate several examples of line forming apparatus.

DETAILED DESCRIPTION OF EXAMPLE EMBODIMENTS

Figure 1:
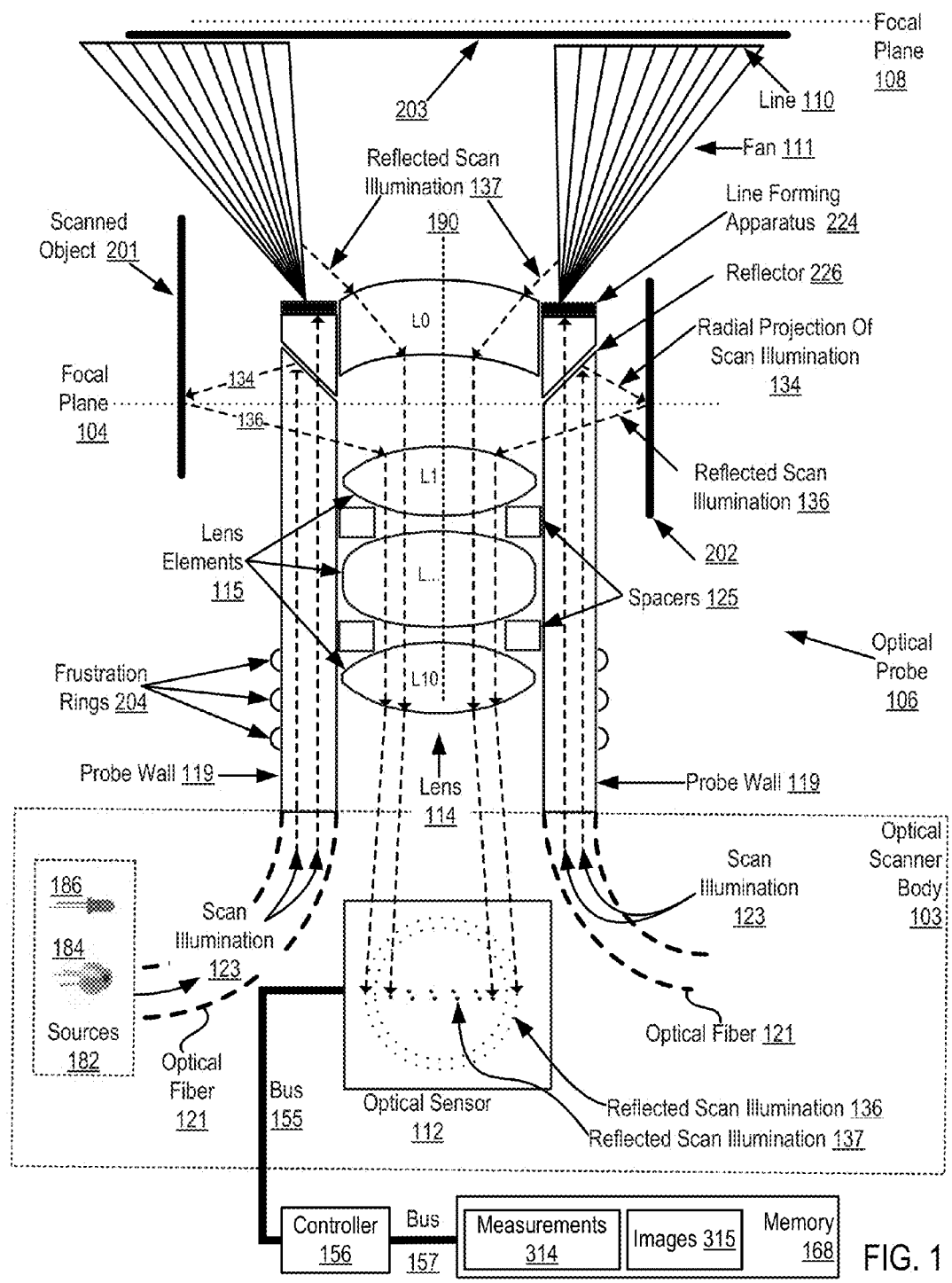
FIGS. 1-3 set forth line drawings and block diagrams of example apparatus for optical scanning

Example apparatus and methods for optical scanning according to embodiments of the present invention are described with reference to the accompanying drawings, beginning with FIG. 1. FIG. 1 sets forth a line drawing and block diagram of example apparatus for optical scanning that includes an optical probe (106), illustrated here in cross-section. The optical probe is capable of movement for optical scanning with respect to both the interior and the exterior of a scanned object (201, 202, 203). In embodiments, the same optical probe can scan aspects of objects of differing size, different hole diameters, different cavity depths, different exterior dimensions, all with the same probe.

The terms 'scan,' scanned,"scanning," and the like, as used here, refer to illuminating a scanned object with scan illumination that is very bright with respect to ambient light levels—so that one or more partial images of the scanned object, portions of the scanned object brightly illuminated by scan illumination, are captured through probe optics and an optical sensor. Apparatus for optical scanning according to embodiments of the present invention typically, or at least optionally, also utilize these partial images to measure certain characteristics of a scanned object or to construct from the partial images a larger or more complete image of a scanned object, including, for example, a 3D image of part or all of a scanned object, interior or exterior.

Optical scanners according to many embodiments of the present invention have the capability of acquiring by imaging and profilometry a "full service profile" of a scanned object. Such a full service profile optionally includes both a high precision 3D scan and also a high precision surface profile of an object. The high accuracy 3D scan achieves microresolution regarding volumetric aspects of an object, that is, linear measurement along volumetric aspects, length, width, circumference, diameter, cavity or hole depths, and so on, with precision on the order of micrometers. The surface profile is effected as optical profilometry, measurements of roughness or smoothness of surfaces, through known methods of focus detection, intensity detection, differential detection, Fourier profilometry, or the like, also typically with precision on the order of micrometers.

One or more scanned objects are represented in the example of FIG. 1 with three drawing elements (201, 202, 203). These three elements are oriented among the apparatus in FIG. 1 so that they could be extended and joined so that the three surfaces upon which scan illumination is project could be three surfaces of an interior of a scanned object. The three surfaces in other embodiments can represent external surfaces of three separate scanned objects, all of which is explained in more detail below, particularly with reference to FIG. 7.

The optical probe includes light conducting apparatus (119) disposed so as to conduct scan illumination (123) from a source (182) of scan illumination through the probe. The light conducting apparatus in this example is a tubular wall of the probe itself, composed of optical glass, quartz crystal, or the like, that conducts scan illumination from a source (182) of such illumination to line forming apparatus (224) or reflecting apparatus (226) in the probe. The scan illumination may be conducted from a source (182) to the probe wall (119) for transmission to a line former or reflector by, as in the example here, optical fiber (121), or through optical glass, a conical reflector, a reflaxicon, and in other ways as will occur to those of skill in the art. The sources (182) themselves may be implemented with LEDs (186), lasers (184), or with other sources of scan illumination as may occur to those of skill in the art.

The optical probe (106) in the example of FIG. 1 includes light reflecting apparatus (226), a 'reflector,' disposed so as to project scan illumination (123) radially (134) away from a longitudinal axis (190) of the probe with at least some of the scan illumination projected onto a scanned object (201, 202). In this example, some of the scan illumination is radially projected (134) and some of the scan illumination is projected in a fan (111) that forms a line (110) upon a scanned object. The reflector (226) can be implemented, for example, as a half-silvered mirror when the scan illumination (123) is all of a same or similar wavelength, so that the portion of the scan illumination that strikes the silvered portion of the mirror is reflected radially. In some embodiments of apparatus for optical scanning according to embodiments of the present invention, however, the scan illumination is of two wavelengths, and the reflector is composed of a layer of dichroic material that reflects one wavelength radially and passes through the other wavelength to line forming apparatus (224) that projects a fan of light into a line on a scanned object.

The example apparatus of FIG. 1 is said to project "at least some" of the radial scan illumination onto a scanned object. In many applications, because of the shape of the particular scanned object, only part of the radial illumination will strike a scanned object and be reflected (136) back into the probe for use in measurements or imaging. And that result is perfectly fine. So long as sufficient reflection (136) is present to support measurement or imaging, there is no need to require all of the radial illumination (134) to strike and reflect from the scanned object back into the probe.

The optical probe (106) in the example of FIG. 1 also includes optical line forming apparatus (224) disposed so as to project scan illumination as a line of scan illumination (110) with at least some of the scan illumination projected onto the scanned object. In some embodiments, scan illumination for optical line forming is collimated, or if not exactly collimated, at least collimated to the extent that most rays of scan illumination are traveling in generally the same direction when they encounter line forming apparatus. In the example of FIG. 1, the probe wall itself (119) and the frustration rings (204) work together by total internal frustration of light rays traveling at angles steep enough to refract through the outer edge of either the probe wall itself or the frustration rings. The frustration rings can be implemented, for example, with an optical epoxy resin whose index of refraction matches the index of refraction of the probe wall. In this way, rays of scan illumination traveling at angles of incidence low enough to reflect back into the probe wall are guided into the refraction rings and refracted out, leaving in the probe wall only those rays of scan illumination traveling in the same direction through the probe wall toward the line forming apparatus. As discussed in more detail below, the line forming apparatus itself can be implemented in a variety of ways, including, for example, Powell lenses, collimators integrated with Powell lenses, refractive lenses, with diffractive optics, and so on.

The optical probe (106) in the example of FIG. 1 also includes a lens (114) disposed so as to conduct, through the probe to an optical sensor (112), scan illumination (136, 137) reflected from a scanned object. The lens (114) is composed of several lens elements (115) and spacers (125) that fit the lens as a whole snuggly into a lens housing formed in this example by the probe wall itself (119). The lens elements (115) include elements L0 through L1, which are configured to effect two focal planes (104, 108). Lens elements L1-L10 effect a focal plane (104) that is disposed with respect to the probe so that the radial projection of scan illumination (134) is in focus where it strikes a scanned object (201, 202). Lens element L0 is an optical field-of-view expander that implements a wide-angle effect for a front view through the lens (114) as a whole. The wide-angle effect of L0 also disposes a second focal plane (108) distally from the front of the probe (106) so that a projected line (110) of scan illumination is in focus where a fan (111) of scan illumination strikes a scanned object (203). Lens elements L0-L10 conduct through the probe to an optical sensor (112) scan illumination (137) reflected from a line (110) of scan illumination projected upon a scanned object (203). Lens elements L1-L10 conduct through the probe to an optical sensor (112) scan illumination (136) reflected from a radial projection (134) of scan illumination upon a scanned object (201, 202). The optical sensor may be implemented as a charged coupled device ('CCD'), as a complementary metal oxide semiconductor ('CMOS') sensor, and in other ways as will occur to those of skill in the art.

The example apparatus of FIG. 1 also includes an optical scanner body (103) with the probe (106) mounted upon the optical scanner body. The optical scanner body has mounted within it the source or sources (182) of scan illumination conductively coupled to the light conducting apparatus. In this example of course, the light conducting apparatus is implemented as the probe body (119), and the conductive coupling between the sources of illumination (182) and the light conducting apparatus (119) is effected with optical fiber (121).

In the example apparatus of FIG. 1, the optical sensor (112) is disposed with respect to the lens (114) so as to receive through the lens scan illumination (136, 137) reflected from a scanned object, and the optical sensor is disposed within the optical scanner body so as to capture, from the scan illumination reflected through the lens from the scanned object, an image of at least a portion of the scanned object. Again it is said 'at least a portion.' Many embodiments of scanning apparatus according to embodiments of the present invention evidence little concern that there is a complete image of a scanned object from any particular capture, because an image of any desired completeness is constructed in such embodiments from a sequence of partial images.

The example apparatus of FIG. 1 also includes a controller (156), coupled to the sensor (112) through data bus (155), with the controller configured to determine from scan illumination (136, 137) received through the lens (114) by the sensor (112) measurements of the scanned object (201, 202, 203). The controller (156) may be implemented as a Harvard architecture microcontroller with a control program in memory (168), a generally programmable Von Neumann architecture microprocessor with a control program in memory (168), field programmable gate array ('FPGA'), complex programmable logic device ('CPLD'), application-specific integrated circuit ('ASIC'), a hard-wired network of asynchronous or synchronous logic, and otherwise as will occur to those of skill in the art.

The controller (156) is coupled through a memory bus (157) to computer memory (168), which in this example is used to store the controller's measurements (314) or captured images (315) of a scanned object. Measurements (314) of a scanned object can include for example:

diameter, circularity, and perpendicularity of drilled or milled holes and other cavities, countersink dimensions, depth and diameter, fastener flushness with respect to a surface of a scanned object, dimensions of milled cavities having irregular internal structures, measurements indicating manufacturing defects in scanned objects, cracks, burrs, or the like, and measurements indicating defects in tools, drill bits, mill heads, and the like, and so on.

Regarding manufacturing defects, the controller in example embodiments is programmed to determine according to image processing algorithms the location of a light source and probe in an image, and the light source and probe are configured for an expected surface finish for material of which a scanned object is composed. If there is a significant deviation in surface finish indicating a crack or if there are burrs, reflected scan illumination does not appear as a radially symmetric on the sensor. Rather it will have significant local variations in its appearance. That these variations are greater than a threshold is an indicator of a manufacturing defect such as a burr or crack. Burrs can also be identified from white light images of the entrance and exit of a drilled or milled cavity because the edge of the cavity will not appear smooth.

Figure 2:
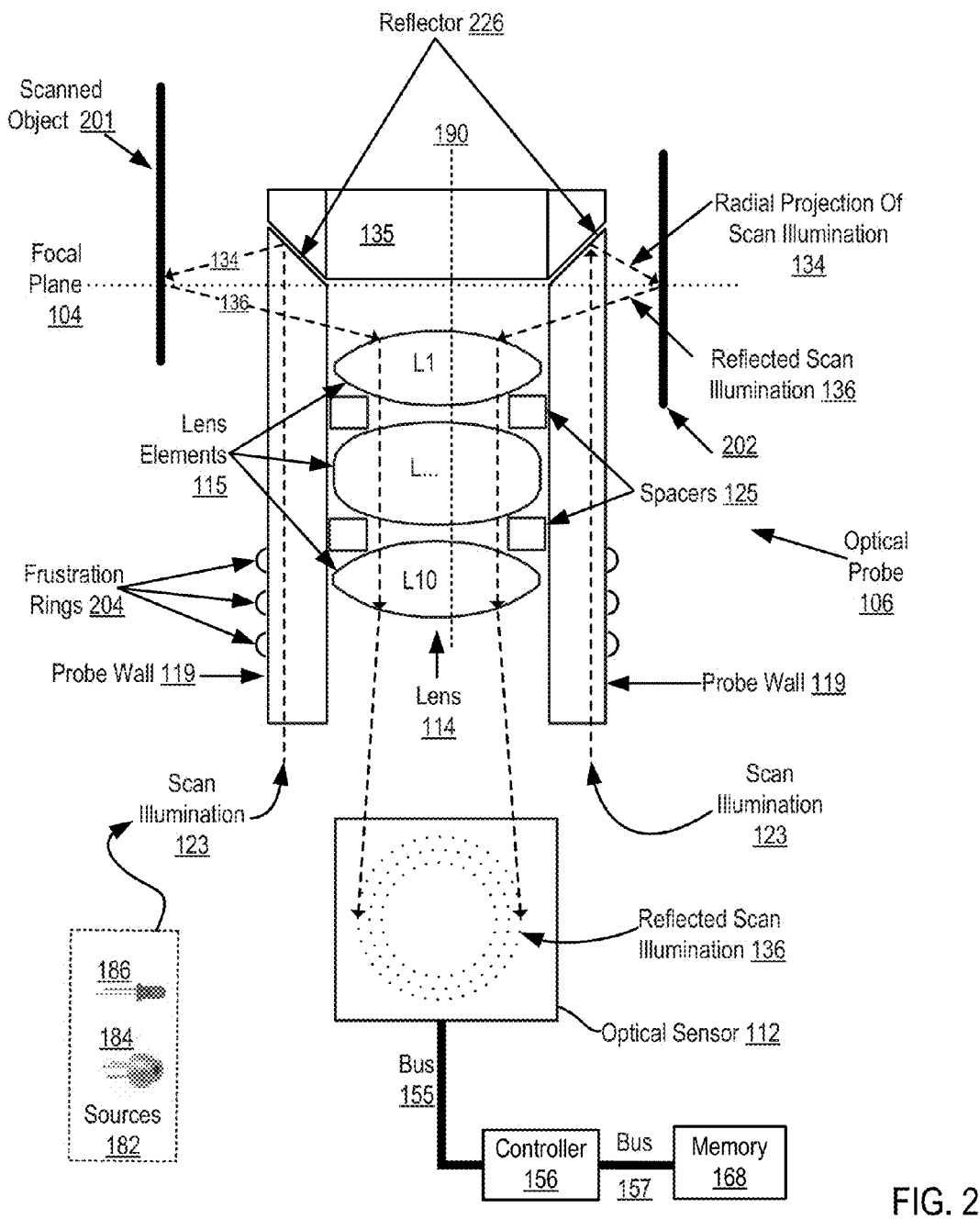

For further explanation, FIG. 2 sets forth a line drawing and block diagram of additional example apparatus for optical scanning The example apparatus of FIG. 2 is very similar to the example apparatus of FIG. 1, except for the exclusion of optical line forming apparatus from the example of FIG. 2. Embodiments that provide radial projection of scan illumination with no provision for optical line forming provide substantial optical scanning and measurement capabilities that are, in some embodiments at least, less expensive to implement than apparatus that includes both line forming and radial projection.

The example apparatus of FIG. 2 includes an optical probe (106), again illustrated in cross-section. The optical probe is capable of movement for optical scanning with respect to both the interior and the exterior of a scanned object (201, 202). One or more scanned objects are represented here with two elements (201, 202). These two elements are illustrated in cross-section so that, extended in three dimensions and joined, they could represent an interior surface of a scanned object. Alternatively, the two surfaces could represent external surfaces of two separate scanned objects, all of which is explained in more detail below.

The optical probe includes light conducting apparatus (119) disposed so as to conduct scan illumination (123) from a source (182) of scan illumination through the probe. The light conducting apparatus in this example is a tubular wall of the probe itself, composed of optical glass, quartz crystal, or the like, that conducts scan illumination from a source (182) of such illumination to line reflecting apparatus (226) in the probe. The scan illumination may be conducted from a source (182) to the probe wall (119) for transmission to a line former or reflector by optical fiber, through optical glass, a conical reflector, a reflaxicon, and in other ways as will occur to those of skill in the art. The sources (182) themselves may be implemented with LEDs (186), lasers (184), or with other sources of scan illumination as may occur to those of skill in the art.

The optical probe (106) in the example of FIG. 2 includes light reflecting apparatus (226), a 'reflector,' disposed so as to project scan illumination (123) radially (134) away from a longitudinal axis (190) of the probe with at least some of the scan illumination projected onto a scanned object (201, 202). The reflector (226) can be implemented, for example, as a sectioned, silvered, optical conical mirror disposed within the probe so that scan illumination that strikes the mirror is reflected radially (134). The example apparatus of FIG. 2 is said to project "at least some" of the radial scan illumination onto a scanned object. In many applications, because of the shape of the particular scanned object, only part of the radial illumination will strike a scanned object and be reflected (136) back into the probe for use in measurements or imaging, a result that is perfectly fine. So long as sufficient reflection (136) is present to support measurement or imaging, there is no need to require all of the radial illumination (134) to strike and reflect from the scanned object back into the probe.

The optical probe (106) in the example of FIG. 2 also includes a lens (114) disposed so as to conduct, through the probe to an optical sensor (112), scan illumination (136) reflected from a scanned object. The lens (114) is composed of several lens elements (115) and spacers (125) that fit the lens as a whole snuggly into a lens housing formed in this example by the probe wall itself (119). The lens elements (115) include elements L1 through L10, which are configured to effect a focal plane (104) that is disposed with respect to the probe so that the radial projection of scan illumination (134) is in focus where it strikes a scanned object (201, 202). Lens elements L1-L10 conduct through the probe to an optical sensor (112) scan illumination (136) reflected from a radial projection (134) of scan illumination upon a scanned object (201, 202).

In the example apparatus of FIG. 2, the optical sensor (112) is disposed with respect to the lens (114) so as to receive through the lens scan illumination (136) reflected from a scanned object, and the optical sensor is disposed so as to capture, from the scan illumination reflected through the lens from the scanned object, an image of at least a portion of the scanned object. The example apparatus of FIG. 2 also includes a controller (156), coupled to the sensor (112) through data bus (155), with the controller configured to determine from scan illumination (136) received through the lens (114) by the sensor (112) measurements of the scanned object (201, 202).

The controller (156) is coupled through a memory bus (157) to computer memory (168), which is used to store the controller's measurement or captured images of a scanned object.

Figure 3:
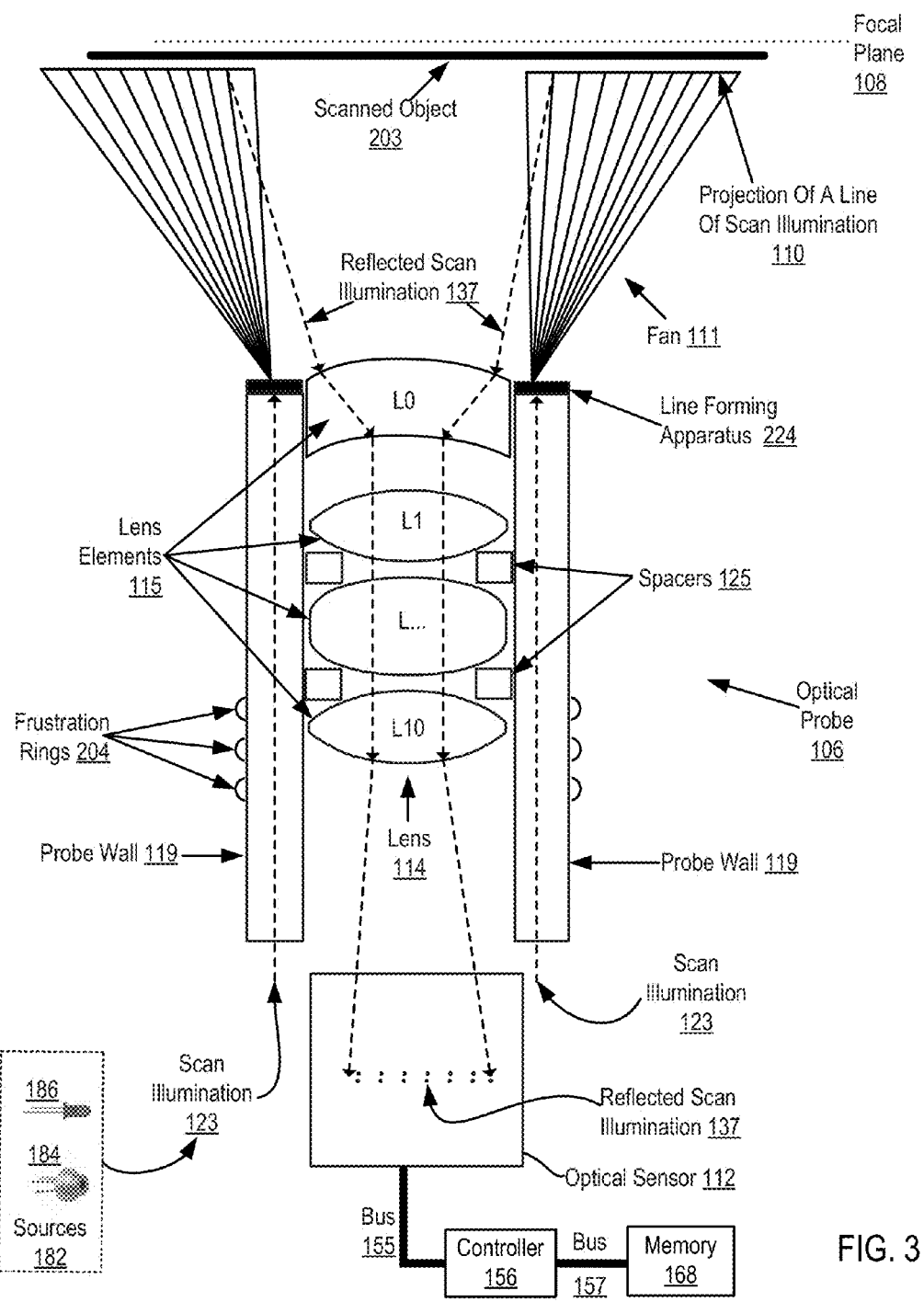

For further explanation, FIG. 3 sets forth a line drawing and block diagram of additional example apparatus for optical scanning The example apparatus of FIG. 3 is very similar to the example apparatus of FIG. 1, except for the exclusion of radial reflection apparatus from the example of FIG. 3. Embodiments that provide distal line projection of scan illumination with no provision for radial projection provide substantial optical scanning and measurement capabilities that are, in some embodiments at least, less expensive to implement than apparatus that includes both line forming and radial projection.

The example apparatus of FIG. 3 includes an optical probe (106), again illustrated in cross-section. The optical probe is capable of movement for optical scanning with respect to both the interior and exterior of a scanned object (203). A scanned object is represented here with one drawing element (203). This element is oriented in FIG. 3 so that it could represent any surface, oriented either on the exterior of a scanned object or as an interior surface, any surface that can be reached by projected scan illumination (111).

The optical probe includes light conducting apparatus (119) disposed so as to conduct scan illumination (123) from a source (182) of scan illumination through the probe. The light conducting apparatus in this example is a tubular wall of the probe itself, composed of optical glass, quartz crystal, or the like, that conducts scan illumination from a source (182) of such illumination to line forming apparatus (224) in the probe.

The scan illumination may be conducted from a source (182) to the probe wall (119) for transmission to a line former by optical fiber, optical glass, a conical reflector, a reflaxicon, and in other ways as will occur to those of skill in the art. The sources (182) themselves may be implemented with LEDs (186), lasers (184), or with other sources of scan illumination as may occur to those of skill in the art.

The optical probe (106) in the example of FIG. 3 also includes optical line forming apparatus (224) disposed so as to project scan illumination as a line of scan illumination (110) with at least some of the scan illumination projected onto the scanned object. In some embodiments, scan illumination for optical line forming is collimated, or if not exactly collimated, at least collimated to the extent that most rays of scan illumination are traveling in generally the same direction when they encounter line forming apparatus. In the example of FIG. 3, the probe wall itself (119) and the frustration rings (204) work together by total internal frustration of light rays traveling at angles steep enough to refract through the outer edge of either the probe wall itself or the frustration rings. The frustration rings can be implemented, for example, with an optical epoxy resin whose index of refraction matches the index of refraction of the probe wall. In this way, rays of scan illumination traveling at angles of incidence low enough to reflect back into the probe wall are guided into the refraction rings and refracted out, leaving in the probe wall only those rays of scan illumination traveling in the same direction through the probe wall toward the line forming apparatus. As discussed in more detail below, the line forming apparatus itself can be implemented in a variety of ways, including, for example, Powell lenses, collimators integrated with Powell lenses, refractive lenses, with diffractive optics, and so on.

The optical probe (106) in the example of FIG. 3 also includes a lens (114) disposed so as to conduct, through the probe to an optical sensor (112), scan illumination (137) reflected from a scanned object. The lens (114) is composed of several lens elements (115) and spacers (125) that fit the lens as a whole snuggly into a lens housing formed in this example by the probe wall itself (119). The lens elements (115) include elements L0 through L10. Lens element L0 is an optical field-of-view expander that implements a wide-angle effect for a front view through the lens (114) as a whole. The wide-angle effect of L0 also disposes a focal plane (108) distally from the front of the probe (106) so that a projected line (110) of scan illumination is in focus where a fan (111) of scan illumination strikes a scanned object (203). Lens elements L0-L10 conduct through the probe to an optical sensor (112) scan illumination (137) reflected from a line (110) of scan illumination projected upon a scanned object (203).

In the example apparatus of FIG. 3, the optical sensor (112) is disposed with respect to the lens (114) so as to receive through the lens scan illumination (137) reflected from a scanned object, and the optical sensor is disposed with respect to the lens so as to capture, from the scan illumination reflected through the lens from the scanned object, an image of at least a portion of the scanned object. The example apparatus of FIG. 3 also includes a controller (156), coupled to the sensor (112) through data bus (155), with the controller configured to determine from scan illumination (137) received through the lens (114) by the sensor (112) measurements of the scanned object (203). The controller (156) is coupled through a memory bus (157) to computer memory (168), which is used to store the controller's measurements or captured images of a scanned object.

Figure 4A:
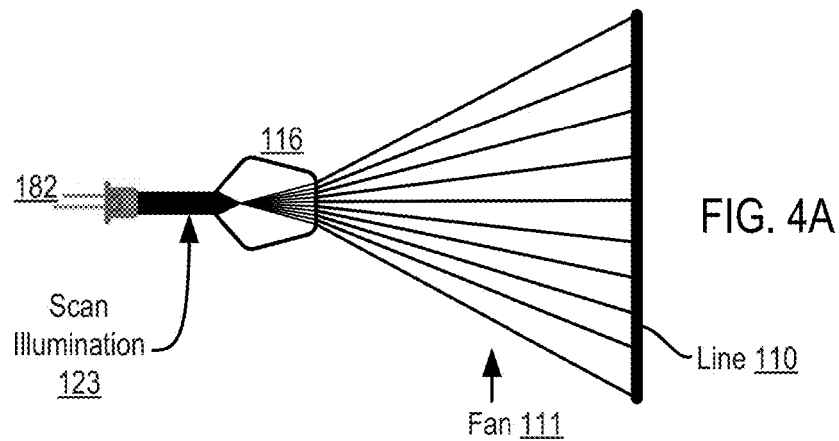
Figure 4B:
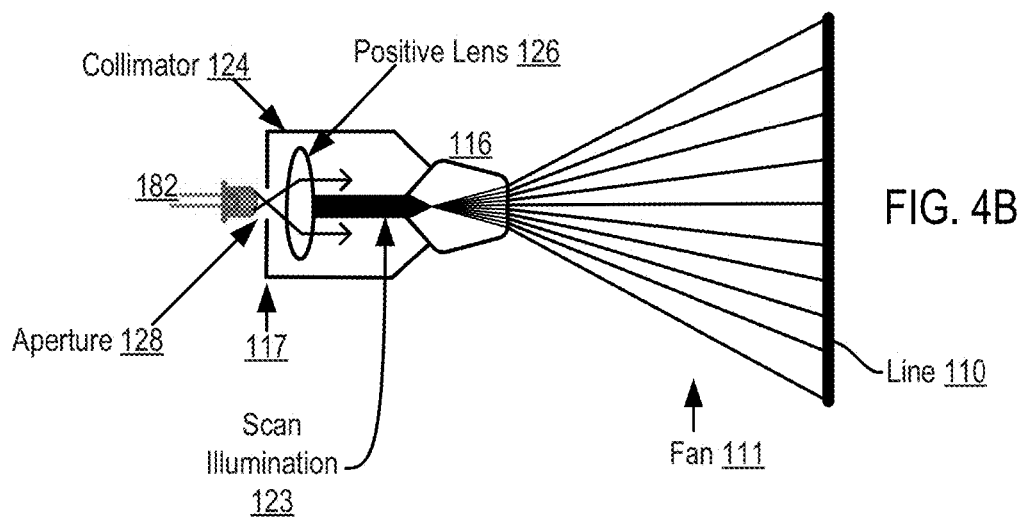
Figure 4C:
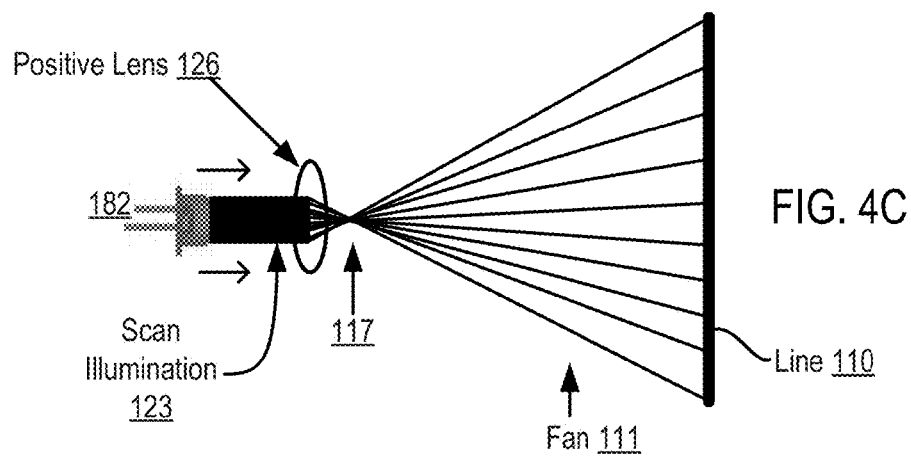

For further explanation of line forming apparatus, FIGS. 4A, 4B, and 4C set forth illustrations of several examples of line forming apparatus. The example apparatus of FIG. 4A includes a Powell lens (116) that forms scan illumination (123) into a fan (111) of illumination that forms a line (110) upon striking a scanned object. A Powell lens, named for its inventor Dr. Ian Powell, is an optical lens formed with an aspheric roof that effects spherical aberration sufficient to distribute scan illumination evenly along a line. The scan illumination (123), as used with the Powell lens in the example of FIG. 1A, is assumed to be either laser light or light that is otherwise collimated upon leaving its source (182). The line (110) for ease of illustration is show here as geometrically straight, although readers will recognize that in fact the actual shape of the line in practical application often will not be perfectly straight, but will conform to the shape of the surface upon which it is projected.

The apparatus in the example of FIG. 4B includes a Powell lens (116) integrated with a collimator (124) that together form scan illumination (123) into a fan (111) of illumination that forms a line (110) upon striking a scanned object. The scan illumination (123), as used with the Powell lens and the collimator in the example of FIG. 1B, is LED light or at least light that is not otherwise collimated when it leaves its source (182). The collimator (124) includes a positive or refractive lens (126) and an aperture (128) situated at a focal point (117) of the lens proximal to the light source, so that rays of light traversing the aperture are refracted by the lens into collimated rays.

The apparatus in the example of FIG. 4C includes a positive or refractive lens (126) that, when illuminated with collimated scan illumination (123), forms the scan illumination into a fan (111) of illumination that forms a line (110) upon striking a scanned object. The scan illumination (123) in this example is laser light or light that is otherwise collimated when or after it leaves its source (182). The lens (126) in this example projects the collimated illumination (123) through a focal point (117) distal from the light source (182) so that rays of light traversing the lens are refracted into a fan (111) that forms a line (110) upon a scanned object.

For further explanation of line forming apparatus, FIGS. 5A and 5B set forth illustrations of further example line forming apparatus. FIG. 5A is a detailed callout of the optical probe of FIG. 5B. The example apparatus of FIGS. 5A and 5B includes a diffractive optic lens (136) that, when illuminated by light (123) from a source of illumination (182) projects scan illumination as a fan (111) disposed at a predetermined angle (140) with respect to a longitudinal axis (190) of an optical probe (106) in which the lens (136) is installed. The angle (140) is determined according to known optical properties of the lens (136), and the longitudinal axis (190) is any axis that is disposed generally in parallel to any center axis of the probe (106).

Figure 6A:
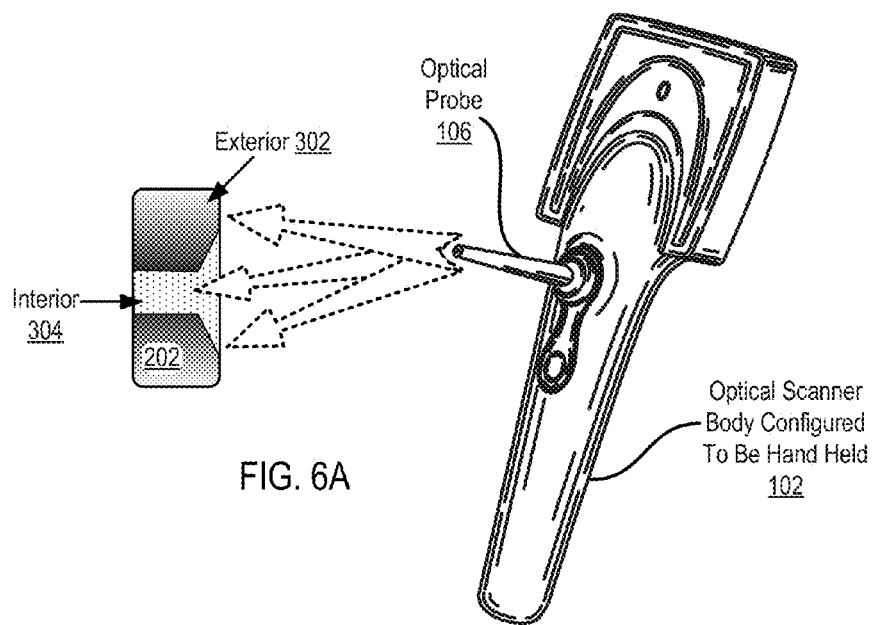
FIGS. 6A and 6B illustrate further example apparatus for optical scanning.

For further explanation, FIG. 6A sets forth a line drawing of example apparatus for optical scanning that includes an optical probe (106) capable of motion for optical scanning with respect to both the interior (304) and the exterior (302) of a scanned object (202). The example apparatus of FIG. 6A includes an optical scanner body (102) with the optical probe (106) mounted upon the optical scanner body. The optical scanner body (102) is configured to be hand held so that the probe (106) is capable of movement by hand for optical scanning with respect to the scanned object, including both movement within the interior (304) of the scanned object (202) and movement with respect to the exterior (302) of the scanned object.

Figure 6B:
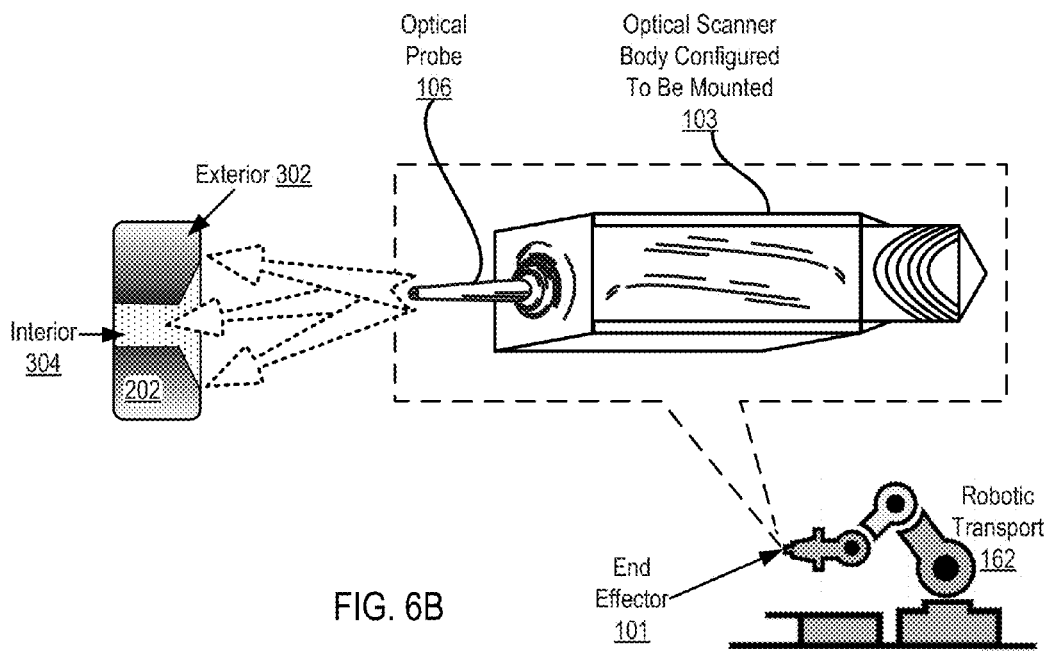

For further explanation, FIG. 6B sets forth a line drawing of example apparatus for optical scanning that includes an optical probe (106) capable of motion for optical scanning with respect to both the interior (304) and the exterior (302) of a scanned object (202). The example apparatus of FIG. 6B includes an optical scanner body (103) with the optical probe (106) mounted upon the optical scanner body. The optical scanner body (103) is configured for mounting upon an end effector (101) of a robotic transport (162) so that the probe is capable of movement by the robotic transport for optical scanning with respect to the scanned object, including both movement within the interior (304) of the scanned object (202) and movement with respect to the exterior (302) of the scanned object.

For further explanation, FIGS. 7A-7E set forth five line drawings of example apparatus for optical scanning each of which includes an optical probe (106) capable of motion for optical scanning with respect to both the interior (304) and the exterior (302) of a scanned object (202). Each of the example apparatus FIGS. 7A-7E includes an optical scanner body (103) with the optical probe (106) mounted upon the optical scanner body. The optical scanner body (103) in each of FIGS. 7A-7E is configured for mounting upon an end effector of a robotic transport or a jig or fixture so that the probe is capable of movement by the transport, jig, or fixture for optical scanning with respect to a scanned object (202), including both movement within the interior (304) of the scanned object and movement with respect to the exterior (302) of the scanned object. Readers will appreciate by now that the scanner body and probe also could be hand held and moved by hand.

Figure 7A:
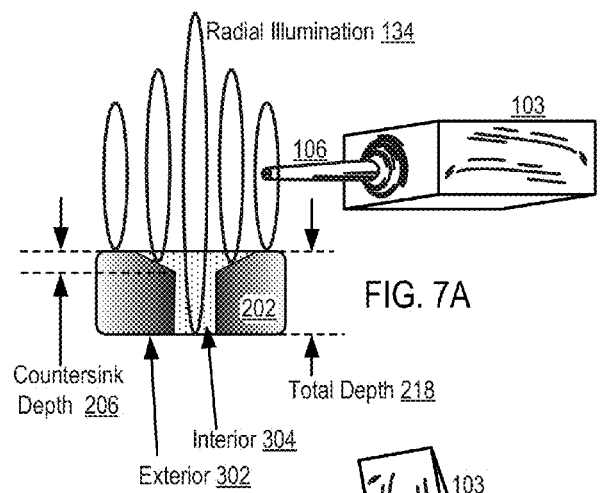
FIGS. 7A-7E set forth five line drawings of example apparatus for optical scanning FIG. 8 sets forth a flow chart illustrating an example method of optical scanning

In the example of FIG. 7A, the scanner body (103) and probe (106) are positioned so that surfaces of the scanned object (202) are illuminated with radial illumination (134) from the probe. When the probe is moved across the top of the scanned object, radial illumination strikes both the exterior (302) and interior (304) of the scanned object in a direction that enables measurement characteristics of interior aspect of the scanned object. In this example, the interior is formed as a hole that is drilled or milled into the scanned object, and the measurements are countersink depth (206) and total depth (218) of the hole.

Figure 7B:
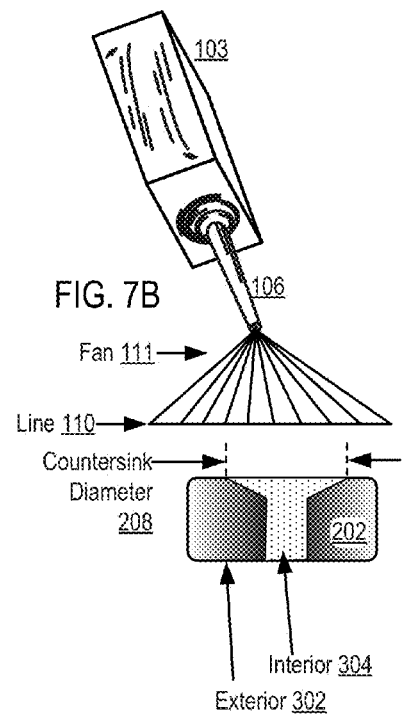

In the example of FIG. 7B, the scanner body (103) and probe (106) are positioned so that surfaces of the scanned object are illuminated with a fan (111) of scan illumination that forms a line (110) when it encounters the scanned object, not a perfectly straight line, but a line that conforms to the surface it strikes. When the probe is moved across the top of the scanned object (202), the fan of illumination strikes both the exterior (302) and the interior (304) of the scanned object in a direction that enables measurement of characteristics of a hole that is drilled or milled into the scanned object, in this example, a measurement of countersink diameter (208).

Figure 7C:
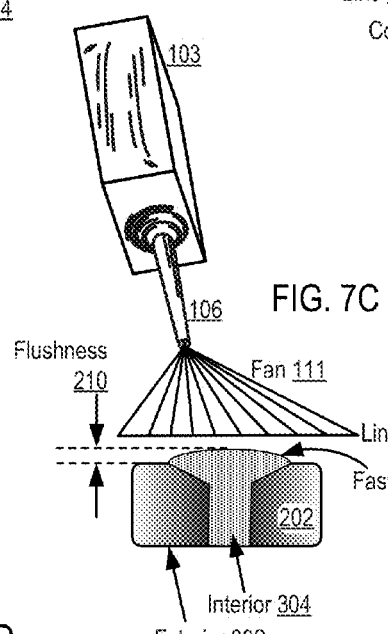

In the example of FIG. 7C, the scanner body (103) and probe (106) are positioned so that surfaces of the scanned object (202) are illuminated with a fan (111) of scan illumination that forms a line (110) when it encounters the scanned object. When the probe is moved across the top of the scanned object, the fan of illumination strikes the exterior of the scanned object, including the top surface of a fastener (216) that is disposed within the a hole drilled or milled into the scanned object. The probe moves in a direction that enables measurement of characteristics of the scanned object, in this example, a measurement of the flushness (210) of the fastener with respect to a top surface of the scanned object.

Figure 7D:
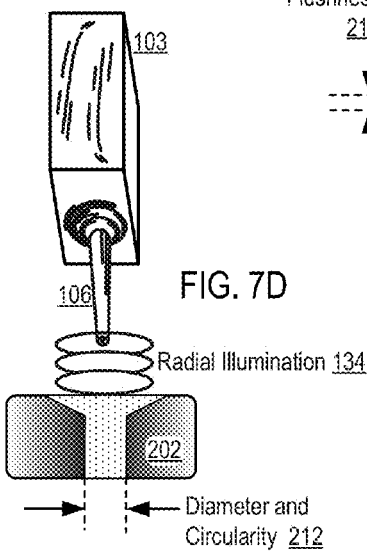

In the example of FIG. 7D, the scanner body (103) and probe (106) are positioned so that interior surfaces of the scanned object are illuminated with radial illumination (134) from the probe. When the probe is moved within the interior of the scanned object (202), radial illumination strikes interior surfaces of the scanned object in a direction that enables measurement of characteristics of the interior. In this example, the measurements are diameter and circularity (212) of a hole that is drilled or milled into the scanned object.

Figure 7E:
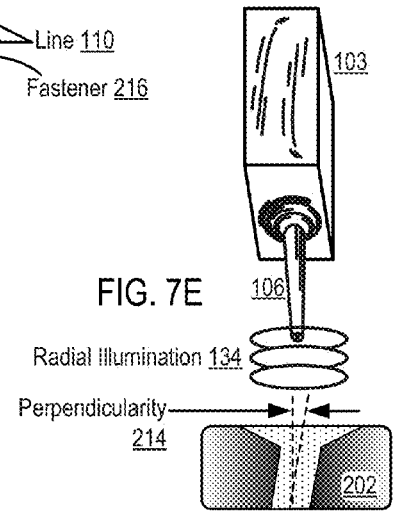

In the example of FIG. 7E, the scanner body (103) and probe (106) are positioned so that interior surfaces of the scanned object are illuminated with radial illumination (134) from the probe. When the probe is moved within the interior of the scanned object, radial illumination strikes interior surfaces of the scanned object in a direction that enables measurement of a characteristic of the interior. In this example, the measurement is perpendicularity (214) of a hole that is drilled or milled into the scanned object.

Figure 8:
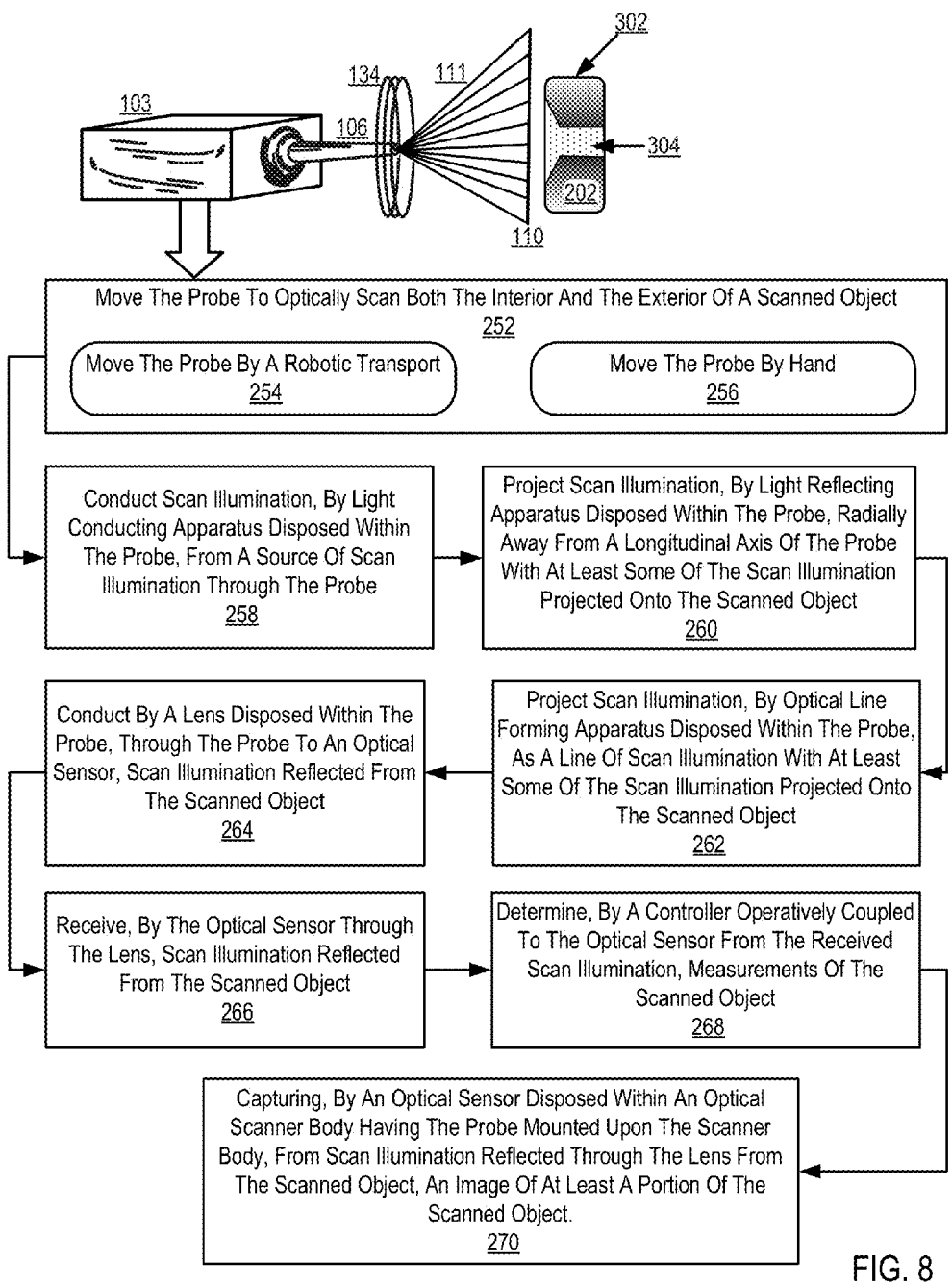

For further explanation, FIG. 8 sets forth a flow chart illustrating an example method of optical scanning with an optical probe (106) that is capable of motion for optical scanning with respect to both the interior and the exterior of a scanned object. In the method of FIG. 8, the optical probe (106) is mounted upon an optical scanner body (103) that houses an optical sensor and one or more sources of scan illumination. This specification uses the apparatus illustrated in FIG. 1 also to explain the method of FIG. 8, so that reference numbers in the following discussion refer to drawing elements both on FIG. 8 and also on FIG. 1.

The method of FIG. 8 includes moving (252) the probe to optically scan both the interior (304) and the exterior (302) of a scanned object (202). Moving the probe can be effected by moving (254) the probe by a robotic transport or by hand (256). Robotic transports include numerically controlled machines as well as devices for computer aided manufacturing. A probe moved by hand can be hand held or held in a jig while the jig is operated by hand.

The method of FIG. 8 includes conducting (258) scan illumination (111, 134), by light conducting apparatus (119) disposed within the probe (106), from a source (182) of scan illumination through the probe. The method of FIG. 8 also includes projecting (260) scan illumination, by light reflecting apparatus (226) disposed within the probe, radially (134) away from a longitudinal axis (190) of the probe with at least some of the scan illumination projected onto the scanned object.

The method of FIG. 8 also includes projecting (262) scan illumination, by optical line forming apparatus (224) disposed within the probe, as a line (110) of scan illumination with at least some of the scan illumination projected onto the scanned object. Projecting (262) scan illumination as a line can be carried out by projecting scan illumination as a fan (111) of scan illumination that projects a line (110) when it encounters a surface of a scanned object, interior or exterior. Projecting (262) scan illumination as a line can also be carried out by projecting scan illumination as a fan (111) of scan illumination disposed at a predetermined angle (140 on FIGS. 5A and 5B) with respect to a longitudinal axis (190) of the probe. Projecting scan illumination as a line can be implemented through a Powell lens, a collimating optical element integrated with a Powell lens, a diffractive optic lens, a refractive optic lens, and no doubt in other ways that will occur to those of skill in the art, all of which are well within the scope of the present invention.

The method of FIG. 8 also includes conducting (264) by a lens (114) disposed within the probe (106), through the probe to an optical sensor (112), scan illumination (136, 137) reflected from the scanned object. The method of FIG. 8 also includes receiving (266), by the optical sensor (112) through the lens (114), scan illumination (136, 137) reflected from the scanned object. The method of FIG. 8 also includes determining (268), by a controller (156) operatively coupled to the optical sensor (112) from the received scan illumination (136, 137), measurements (314) of the scanned object. The method of FIG. 8 also includes capturing (270), by an optical sensor (112) disposed within an optical scanner body with the probe mounted upon the scanner body, from scan illumination (136, 137) reflected through the lens (114) from the scanned object (201, 202, 203), one or more images (315) of at least a portion of the scanned object.

Example embodiments of the present invention are described largely in the context of fully functional apparatus for optical scanning Readers of skill in the art will recognize, however, that the present invention also may be embodied in one or more methods of use, methods of manufacture, and in a computer program product disposed upon computer readable storage media for use with any suitable data processing system. Such computer readable storage media may be any storage medium for machine-readable information, including magnetic media, optical media, or other suitable media. Examples of such media include magnetic disks in hard drives or diskettes, compact disks for optical drives, magnetic tape, and others as will occur to those of skill in the art. Persons skilled in the art will immediately recognize that any computer system having suitable programming means will be capable of executing the steps of the method of the invention as embodied in a computer program product. Persons skilled in the art will recognize also that, although some of the example embodiments described in this specification are oriented to software installed and executing on computer hardware, nevertheless, alternative embodiments implemented as firmware or as hardware are well within the scope of the present invention. The flowcharts and block diagrams in the Figures illustrate the architecture, functionality, and operation of possible implementations of computer apparatus, methods, and computer program products according to various embodiments of the present invention.

It will be understood from the foregoing description that modifications and changes may be made in various embodiments of the present invention without departing from its true spirit. The descriptions in this specification are for purposes of illustration only and are not to be construed in a limiting sense. The scope of the present invention is limited only by the language of the following claims.

What is claimed is:

1. Apparatus for optical scanning, the apparatus comprising an optical probe capable of motion for optical scanning with respect to both the interior and the exterior of a scanned object, the optical probe comprising:

light conducting apparatus disposed so as to conduct scan illumination from a source of scan illumination through the probe;

optical line forming apparatus disposed so as to project scan illumination as a line of scan illumination with at least some of the scan illumination projected onto the scanned object; and light reflecting apparatus disposed so as to project the scan illumination radially away from a longitudinal axis of the probe with at least some of the scan illumination projected onto the scanned object;

a lens disposed so as to conduct, through the probe to an optical sensor, scan illumination reflected from the scanned object;

the apparatus further comprising an optical scanner body having the probe mounted upon the optical scanner body with the optical scanner body configured for mounting upon an end effector of a robotic transport so that the probe is capable of movement by the robotic transport for optical scanning with respect to the scanned object, including both movement within the scanned object and movement with respect to the exterior of the scanned object.

2. The apparatus of claim 1 wherein optical line forming apparatus further comprises the optical line forming apparatus disposed so as to project scan illumination as a fan of scan illumination.

3. The apparatus of claim 1 wherein optical line forming apparatus further comprises the optical line forming apparatus disposed so as to project scan illumination as a fan of scan illumination disposed at a predetermined angle with respect to a longitudinal axis of the probe.

4. The apparatus of claim 1 wherein the optical line forming apparatus further comprises a Powell lens.

5. The apparatus of claim 1 wherein the optical line forming apparatus further comprises a collimating optical element integrated with a Powell lens.

6. The apparatus of claim 1 wherein the optical line forming apparatus further comprises a diffractive optic lens.

7. The apparatus of claim 1 wherein the optical line forming apparatus further comprises a refractive optic lens.

8. The apparatus of claim 1 further comprising
the optical sensor disposed with respect to the lens so as to receive through the lens the scan illumination reflected from the scanned object; and
a controller operatively coupled to the optical sensor, the controller configured to determine from the received scan illumination measurements of the scanned object.

9. The apparatus of claim 1 further comprising an optical scanner body with the probe mounted upon the optical scanner body, the optical scanner body comprising:
the source of scan illumination conductively coupled to the light conducting apparatus; and
the optical sensor disposed within the optical scanner body so as to capture, from the scan illumination reflected through the lens from the scanned object, an image of at least a portion of the scanned object.

10. Apparatus for optical scanning, the apparatus comprising an optical probe capable of motion for optical scanning with respect to both the interior and the exterior of a scanned object, the optical probe comprising:

light conducting apparatus disposed so as to conduct scan illumination from a source of scan illumination through the probe;

light reflecting apparatus disposed so as to project the scan illumination radially away from a longitudinal axis of the probe with at least some of the scan illumination projected onto the scanned object; and a lens disposed so as to conduct, through the probe to an optical sensor, scan illumination reflected from the scanned object.

11. The apparatus of claim 10 further comprising the optical sensor disposed with respect to the lens so as to receive through the lens the scan illumination reflected from the scanned object; and a controller operatively coupled to the optical sensor, the controller configured to determine from the received scan illumination measurements of the scanned object.

12. The apparatus of claim 10 further comprising an optical scanner body with the probe mounted upon the optical scanner body, the optical scanner body comprising:

the source of scan illumination conductively coupled to the light conducting apparatus; and the optical sensor disposed within the optical scanner body so as to capture, from the scan illumination reflected through the lens from the scanned object, an image of at least a portion of the scanned object.

13. The apparatus of claim 10 further comprising an optical scanner body having the probe mounted upon the optical scanner body with the optical scanner body configured for mounting upon an end effector of a robotic transport so that the probe is capable of movement by the robotic transport for optical scanning with respect to the scanned object, including both movement within the scanned object and movement with respect to the exterior of the scanned object.

14. The apparatus of claim 10 further comprising an optical scanner body having the probe mounted upon the optical scanner body with the optical scanner body configured to be hand held so that the probe is capable of movement by hand for optical scanning with respect to the scanned object, including both movement within the scanned object and movement with respect to the exterior of the scanned object.

15. Apparatus for optical scanning, the apparatus comprising an optical probe capable of motion for optical scanning with respect to both the interior and the exterior of a scanned object, the optical probe comprising:

light conducting apparatus disposed so as to conduct scan illumination from a source of scan illumination through the probe;

light reflecting apparatus disposed so as to project scan illumination radially away from a longitudinal axis of the probe with at least some of the scan illumination projected onto the scanned object;

optical line forming apparatus disposed so as to project scan illumination as a line of scan illumination with at least some of the scan illumination projected onto the scanned object; and a lens disposed so as to conduct, through the probe to an optical sensor, scan illumination reflected from the scanned object.

16. The apparatus of claim 15 wherein optical line forming apparatus further comprises the optical line forming apparatus disposed so as to project scan illumination as a fan of scan illumination.

17. The apparatus of claim 15 wherein optical line forming apparatus further comprises the optical line forming apparatus disposed so as to project scan illumination as a fan of scan illumination disposed at a predetermined angle with respect to a longitudinal axis of the probe.

18. The apparatus of claim 15 wherein the optical line forming apparatus further comprises a Powell lens.

19. The apparatus of claim 15 wherein the optical line forming apparatus further comprises a collimating optical element integrated with a Powell lens.

20. The apparatus of claim 15 wherein the optical line forming apparatus further comprises a diffractive optic lens.

21. The apparatus of claim 15 wherein the optical line forming apparatus further comprises a refractive optic lens.

22. The apparatus of claim 15 further comprising the optical sensor disposed with respect to the lens so as to receive through the lens the scan illumination reflected from the scanned object; and a controller operatively coupled to the optical sensor, the controller configured to determine from the received scan illumination measurements of the scanned object.

23. The apparatus of claim 15 further comprising an optical scanner body with the probe mounted upon the optical scanner body, the optical scanner body comprising:

the source of scan illumination conductively coupled to the light conducting apparatus; and the optical sensor disposed within the optical scanner body so as to capture, from the scan illumination reflected through the lens from the scanned object, an image of at least a portion of the scanned object.

24. The apparatus of claim 15 further comprising an optical scanner body having the probe mounted upon the optical scanner body with the optical scanner body configured for mounting upon an end effector of a robotic transport so that the probe is capable of movement by the robotic transport for optical scanning with respect to the scanned object, including both movement within the scanned object and movement with respect to the exterior of the scanned object.

25. The apparatus of claim 15 further comprising an optical scanner body having the probe mounted upon the optical scanner body with the optical scanner body configured to be hand held so that the probe is capable of movement by hand for optical scanning with respect to the scanned object, including both movement within the scanned object and movement with respect to the exterior of the scanned object.

* * * * *